United States Patent
Christie et al.

(10) Patent No.: US 6,245,323 B1
(45) Date of Patent: Jun. 12, 2001

(54) BONDED METAL HYDROXIDE-ORGANIC COMPOSITE POLYMER FILMS ON PARTICULATE SUBSTRATES

(75) Inventors: James D. Christie, Yonkers; William C. Howard, Yorktown Heights, both of NY (US)

(73) Assignee: Engelhard Corporation, Iselin, NJ (US)

( * ) Notice: Subject to any disclaimer, the term of this patent is extended or adjusted under 35 U.S.C. 154(b) by 0 days.

(21) Appl. No.: 09/579,958

(22) Filed: May 26, 2000

(51) Int. Cl.$^7$ .................................................. A61K 7/021
(52) U.S. Cl. ........................... 424/63; 424/64; 424/489; 427/388.1; 427/458; 428/402; 428/403; 523/200; 514/844; 106/415
(58) Field of Search ............................... 424/489, 64, 63; 106/415; 428/402, 403; 427/458; 523/200

(56) References Cited

U.S. PATENT DOCUMENTS

| | | | |
|---|---|---|---|
| 3,986,007 | 10/1976 | Ruoff, Jr. ........................... | 235/151 |
| 4,116,628 | 9/1978 | Hesse et al. ........................ | 427/154 |
| 4,205,997 | 6/1980 | Hesse et al. ........................ | 106/308 |
| 4,323,554 | 4/1982 | Bernhard .............................. | 424/63 |
| 5,236,989 | 8/1993 | Brown et al. ....................... | 524/413 |
| 5,268,197 | 12/1993 | Pons et al. .......................... | 427/221 |
| 5,378,275 | 1/1995 | Shiraga et al. ..................... | 106/417 |
| 5,609,911 | 3/1997 | Okabe et al. ....................... | 427/212 |
| 5,824,144 | * 10/1998 | He et al. ............................. | 106/403 |
| 5,885,342 | * 3/1999 | Gale et al. .......................... | 106/417 |

* cited by examiner

Primary Examiner—Thurman K. Page
Assistant Examiner—Rachel M. Bennett
(74) Attorney, Agent, or Firm—Ostrolenk, Faber, Gerb & Soffen, LLP

(57) ABSTRACT

A lamellar particle is coated with an amorphous metal oxide hydrated gel which is then converted into a hydrophobic metal hydroxide-organic composite polymer film. The resulting product can be combined with a powdery film-forming polymer to produce a film-forming composition which can be applied by electrostatic coating. It also has significantly enhanced performance in plastic masterbatching, hydrophobic cosmetic formulations, and liquid paints and numerous other applications where a hydrophobic pigment is advantageous.

32 Claims, No Drawings

BONDED METAL HYDROXIDE-ORGANIC COMPOSITE POLYMER FILMS ON PARTICULATE SUBSTRATES

BACKGROUND OF THE INVENTION

The application of coatings on various substrates by an electrostatic coating process is well known. For example, many automotive finishes are applied by such a method. The composition applied by this process is an electrically chargeable powder mixture of a film forming polymer containing a pigment or pigments of the desired color, as well as other processing additives. The preparation of such powder coating compositions for application by powder coating spraying applicators has presented a problem in the past with platy pigments.

Pigments which are composed of platelets rely on their lamellar structure for their maximum appearance effect. Examples of such platelets include metallic flakes such as aluminum flakes, bronze flakes, and stainless steel flakes and natural or synthetic pearlescent pigments exemplified by, for instance, natural pearlescence or a metal oxide-coated mica such as titanium dioxide-coated mica, reduced titanium dioxide-coated mica and iron oxide-coated mica, and titanium and/or iron oxide coated glass flakes, iron oxide coated aluminum flakes, metal-oxide coated silica flake, alumina flake and graphite flake, bismuth oxychloride, and optically variable pigments. In the course of the manufacture of powder coating compositions containing such metallic or pearlescent pigments, the lamellar structure is destroyed during the extrusion or grinding processes which are used to incorporate non-platy materials into the resin system. As a result, the resulting finish exhibits a reduced luster effect.

In order to avoid the foregoing problem, the industry has dry blended the pigments and polymer powder, i.e., the powder carrier is mechanically blended with the pigments. Unfortunately, the pigment and powder coating particles have significantly dissimilar surface energies and particle sizes and therefore they do not mix readily or remain well dispersed during spray-out. In addition, the pigments are normally metal oxides, which always retain a hydrous film that drastically inhibits surface charge retention.

A bonding process was developed to overcome the problems encountered as a result of the dry blending process. In the bonding process, the powder base and pigment are mixed together and then heated to a temperature sufficient to soften the surface of the powder particles so that the resin particles can adhere to the surface of the pigment particles. The process works reasonably well for corona electrostatic charging applications. Unfortunately, it still leaves two distinctly different surfaces remaining in the final mixture, namely the powder surface and the surface of the laminar pigment that are now agglomerated to some degree. It does not work well for tribo electrostatic charging systems. This process also requires additional processing steps to prepare the powder coating composition and also it must be especially adapted to each selected combination of pigment and powder base.

U.S. Pat. No. 5,378,275 discloses a mica pigment-containing water base paint composition which is the combination of a water soluble or water dispersable film forming polymer and a mica-containing pigment. The mica pigment can be mica flakes or metal oxide-coated mica flakes which have been uniformly coated with a melamine resin by slurring and then volatilizing the organic solvent present.

U.S. Pat. Nos. 4,116,628 and 4,205,997 disclose powdery pearlescent pigment compositions which are coated with a solid polymer in order to protect the pigment prior to use.

A method of coating inorganic and organic particles such as pigment particles and colorant particles with a plastic dispersion is disclosed in U.S. Pat. No. 5,268,197.

A powder coating composition is disclosed in U.S. Pat. No. 3,986,007 in which synthetic resins, hardeners and pigments such as metals, metal alloys and mica for coatings with a metallic appearance are prepared by a process in which the individual components are mixed in a finely divided state under an atmosphere of a protective gas and the mixture is plasticized with homogenization at a temperature at which the viscosity of the synthetic resin is higher than the drop viscosity.

An improvement over the foregoing prior art is set forth in U.S. Pat. No. 5,824,144. A process is described in which the metal platelets are provided with a viscous surface layer of polymer or "sticky" liquid material. When this treated pigment is blended with powder coating compositions, the powder agglomerates to the surface of the pigment thereby minimizing color separation. The coating results in a better charge on those coated pigment particles which do not become attached to the powder materials, i.e., they accept a charge which is closer to the charge on the powder coating particle surfaces than the uncoated pigment particles. While this process represents an advance over the art, further improvements are desired.

An improved method and product has now been discovered. Advantageously, it is not limited to pigments but is applicable to any laminar platelet. In addition, the method allows the surface energy of the product to be significantly lowered in a controlled manner so that the pigment exhibits a hydrophobic surface that is now compatible with the formulation. This hydrophobic surface facilitates use of this product in many other applications in which pearlescent pigments are employed. Examples include, but are not limited to, incorporation into plastic articles, e.g., making masterbatches, "long-wear" and oil based cosmetic formulations and weather resistant exterior coatings.

It is the object of the present invention to provide a new process for preparing platelets having hydrophobic surface characteristics making them more suitable for incorporation into various formulations, in particular powder coating compositions suitable for corona and tribo electrostatic applications and formulations requiring hydrophobic surface properties. This and other objects of the invention will become apparent to those skilled in the art from the following detailed description.

SUMMARY OF THE INVENTION

This invention relates to a platelet suitable for incorporation into various hydrophobic formulations such as a powder coating applications, cosmetic formulations, plastic masterbatching and exterior paints, among other applications. More particularly, laminar platelets are provided with a hydrophobic surface layer of a stable partly dehydrated metal hydroxide-organic composite. For powder coating formulations, the surface coating results in a pigment surface very similar in energy and chargeability to the resin (polymer) film former. The pigment is now easily dry blended and remains well dispersed during the entire coating procedure, including film formation and over-spray recycling.

DESCRIPTION OF THE INVENTION

In accordance with the present invention, a lamellar particle such as a platelet-like pigment or platelet-like filler is provided with a hydrophobic surface layer of partly dehydrated metal hydroxide organic composite. The platelets can be made of a natural substance such as mica or kaolin or of a reflective metal such as aluminum flakes, silver flakes, bronze flakes, stainless steel flakes or any natural or synthetic pearlescent pigment. Natural pearlescent pigments include natural pearlescence and synthetic pigments include metal oxide-coated mica pigments, titanium and/or iron oxide coated glass flakes, iron coated aluminum flakes and reduced titanium dioxide coated micas metal-oxide coated silica flake, alumina flake and graphite flake, bismuth oxychloride, and optically variable pigments. At the present time, the most popular synthetic pigments are the titanium dioxide-coated micas and iron oxide-coated micas. Any of these lamellar pigments or fillers can be treated in accordance with the present invention.

The lamellar particles are provided with the surface coating of metal hydroxide organic composite polymer by partly dehydrating an amorphous metal oxide hydrated gel containing organic acids and/or sulfates.

The coated lamellar particles are prepared by simply combining the solid lamellar material with a gel-forming material under gel forming conditions and then reacting the gel with said organics. Conveniently, the particles can be slurried in an aqueous medium to which a gel forming metal salt is present or is added. In general, the slurry will contain about 0.1–40% of the particles and preferably about 5–30% particulate material. Any metal ion (or mixture of metal ions) which forms a hydroxide gel can be employed. Metals in Group III of the Periodic Table such as aluminum, cerium, yttrium and the lanthanides are preferably employed although other metals which can exhibit a +2, +4 and preferably a +3 valence state such as iron are also usable. In general, the metal ion will constitute about 0.1–10 wt %, preferably about 0.5–5 wt % of the slurried pigment weight. The pH of the slurry can be adjusted with acid such as HCl or base such as NaOH to facilitate the gel forming hydrolysis reaction. It is also preferred to agitate the mixture to a degree sufficient so that all of the surfaces of the platelets are exposed. The amorphous metal oxide hydrated gel will generally constitute about 0.1–10 weight percent of the pigment, and preferably about 0.3–3%. After the agitation is continued for a suitable length of time, which generally is about 0.2–5 hours and preferably about 0.5–2 hours, a water soluble organic acid or salt is combined with the resulting positively charged hydroxide gel film on the pigment surface.

The organic acid or salt can be an amino acid, fatty acid, benzoic acid, alkylsulfate or the like. Any water soluble organic agent which reacts with the gel in the ambient environment to form a stable insoluble metal hydroxide organic salt film can be employed. As used herein, stable refers to non-dissociation in water at all but the most extreme pHs. Multivalent metal salts of organic acids typically do not dissociate easily. The coating, therefore, does not decompose in the usual pigment applications. Non-limiting examples of the acids and salts include lauryl sulfate, lauric acid, sulfanilic acid, L-glutamine, L-phenylalanine, and the agent can be a single substance or combination of substances. The organic acid or salt is generally used in the form of an aqueous solution. Generally, the organic agent will constitute about 0.1 to 10 weight percent of the pigment weight and preferably about 0.25–5%.

The resulting metal hydroxide-organic composite polymer film is then bonded to the particle by partial dehydration of the film onto the particle surface. This partial dehydration effects removal of all surface water while still retaining the hydroxyl character of the metal. This is accomplished by recovering the coated particle from the slurry by any convenient means, such as filtering, optionally washing the recovered material and drying the product at, for example, 80 to 150 degrees for 1 to 16 hours. The degree of dehydration is not critical as long as it is sufficient to result in the desired bonding.

The resulting coated particles can then be incorporated into a conventional powder coating composition for electrostatic application by dry blending. The platelet surface now exhibits a surface energy which is similar to that of the powder coating particles. That surface energy also results in pigments with significantly improved flow properties which can be exploited in other applications such as plastic masterbatches and the like.

The metal hydroxide-organic composite hydrophobic films exhibit a very low surface energy with improved flowability, that is easily and stably dispersed in polymer matrices. The low surface energy platelets are also more compatible with the cross-linking polymer with which they are combined during the film forming of the coating. Importantly, the hydrophobic surface readily accepts a static charge whereas prior to the formation of the film, the hydrous layer significantly reduces the particle's ability to orient during baking or accept the static charge. The change in the surface energy can be regulated to give a value similar to the surface energy of the powder resin by appropriate selection of the reagent used during the particulate's formation. Two powders with the same surface energy will not display an appreciable interfacial tension and will mix with each other as a dry blend at a very low shear. By improving the flow of the particles, the probability of separation of the coated particle from the powdered resin when a mixture is being sprayed through the application equipment becomes significantly lessened. The pigments also remain well dispersed during capture and recycling of powder over-spray collected from the initial spray-out. Thus, the surface treatment allows the particles to be mixed more easily, flow exceptionally in the powder coating air stream, orient during film-formation, be readily chargeable in static charging ("tribo") applications and be used for over-spray recycling systems.

The performance of lamellar fillers and effect pigments in many cosmetic applications is improved with the increasing hydrophobicity of the particle. Particulate substrates with hydrophobic properties are used in cosmetics as an inexpensive filler. By increasing the degree of hydrophobicity, pigments or fillers have improved wear, sweat resistance and tactile properties. The hydrophobic coating makes the particles more lipophilic and they can therefore be dispersed in the continuous phase of a water-in-oil emulsion and will not migrate to the water and droplet interfaces. Use of amino acids as the organic agent has the added value of providing skin moisturizing properties and resulting in a product with increased suspendability in many liquid formulations. Another advantage of the invention is that the product can be produced from naturally occurring materials which are abundantly used not only in cosmetics but also in the food and drug industry. Hydrophobic pigments do not attract atmospheric water as do untreated metal-oxide surfaces. The resulting pigments can be used in weather resistant exterior coatings. There are numerous other applications of hydrophobic pigments.

In order to further illustrate the invention, various examples are set forth below. In these, as throughout the rest of this specification and claims, all parts and percentages are by weight and all temperatures in degrees Centigrade unless otherwise indicated.

EXAMPLE 1

A 10% slurry of a commercially available titanium dioxide-coated mica pearlescent pigment in distilled water is placed into a Morton flask. The slurry is stirred at 300 rpm and heated to 75° C. The pH of the slurry is adjusted to 3.0 with 20% HCl, 1.2 weight percent of aluminum 2 0 hydroxide (as a 60% aluminum nitrate solution) is added together with sulfanilic acid. An amount of 1% aqueous solution of lauric acid is added slowly to the slurry until a lauric acid concentration of 1.5% is achieved and then allowed to stir for 30 minutes. The sample is filtered, washed thoroughly, dried at 120° C. for 16 hours.

The flowability of the resulting product was examined using a Hosokawa Micron Corp. Powder Tester Model PT-N. On a scale of 0 (poorest) to 100 (best), the flowability index was 55 while that of the pigment before the treatment was 39. The flowability index is a composite value derived from the following measurements: Angle of Repose, Compressibility, Angle of Spatula, Uniformity and Cohesion as set forth in the users manual of the Hosokawa instrument.

EXAMPLE 2

A 10% slurry of kaolin in distilled water is placed into a Morton flask. The slurry is stirred at 300 rpm and heated to 50° C. The pH of the slurry is adjusted to 3.0 with 20% HCl, 4.5 weight percent of aluminum hydroxide (as a 60% aluminum nitrate solution) is added together with 3.0 wt % of L-phenylalanine. A 3% quantity of lauric acid is added slowly as a 1% solution and allowed to stir for 30 minutes. The sample is filtered, washed thoroughly, dried at 120° C. for 2 hours. The product displayed improved performance in hydrophobic cosmetic formulations.

EXAMPLE 3

A 10% slurry of mica in distilled water is placed in a Morton flask. The slurry is stirred at 300 rpm and heated to 65° C. The pH of the slurry is adjusted to 2.0 with 20% HCl, and 3.0 weight percent of aluminum hydroxide (as a 60% aluminium chloride solution) is added together with 2.0 weight percent alanine. A 4% quantity of lauryl sulfate is added slowly as a 5% solution and allowed to stir for two hours. The sample is filtered, washed thoroughly and dried at 120° C. for 8 hours. The product displayed improved performance in hydrophobic cosmetic formulations.

EXAMPLE 4

Example 2 is repeated except that DL-glutamine is used instead of the L-phenylalanine and is added to a concentration of 3%. The product displayed improved performance in hydrophobic cosmetic formulations.

EXAMPLE 5

Example 2 is repeated except that a titanium dioxide-coated mica is used as the pigment instead of the kaolin. The increased hydrophobicity is seen in that the treated pigment had a contact angle with water of 160° while the untreated pigment had a contact angle of 21°.

EXAMPLE 6

A 10% slurry of pearlescent pigment used in Example 1 in distilled water is placed into a Morton flask. The slurry is stirred at 300 rpm and heated to 60° C. The pH of the slurry is adjusted to 3.0 with 20% HCl, 0.8 weight percent of aluminum hydroxide (as a 60% aluminum nitrate solution) is added together with L-phenylalanine. A 3% concentration of lauryl sulfate is achieved by adding it slowly as a 1% solution and stirring for 30 minutes. The sample is filtered, washed thoroughly, dried at 120° C. for 2 hours.

EXAMPLE 7

A powder coating formulation was prepared by dry blending 8 parts of a pigment with 92 parts of a commercially available powder coating formulation (TGIC-Free Resin) and used to coat a metal panel by corona spray application. The attraction of the powder coating formulation to the panel was considerably increased with the treated pigment of Example 1 compared to the untreated pigment. The evaluation was by visual examination. The metal panel also has better reflectance and smoothness because the pigment of the invention wets-out better in the powder coating formulation.

EXAMPLE 8

Pigment was evaluated in a recycle test as follows: An 8% loading of $TiO_2$ coated mica pigment with an average particle size of 10 μm in TGIC-free Powder Resin was prepared by dry blending and Benda-Lutz bonding(the current industry standard for incorporation of pearlescent pigments into powder coatings). For comparison, a commercially available exterior grade pigment was also tested. Evaluation of the results were done by determination of the percent pigment left in the sample after 4 recycles and by visual and instrumental evaluation of the appearance change of finished panels. A black resin was used with white pearl pigment so the differences in the white to black color measurement indicate how much white pearl pigment remains in the sample after each recycle. This recycle test indicates that the treated pearlescent pigment incorporated into the resin by dry blending performed better than the Benda-Lutz bonded samples.

A white pearlescent pigment coated pursuant to this invention was dry blended with black TGIC-free powder coating resin at an 8% loading by weight. Additionally, an exterior grade white pearlescent pigment was bonded by the Benda-Lutz method with the same black TGIC-free powder coating resin at the same 8% loading by weight. The bonded sample is the current industry standard for incorporation of pearlescent pigments into powder coating formulations. These samples were used in the above recycle test with the following results:

| Sample | Percent Reflectance Retained from Initial Recycle | | | |
|---|---|---|---|---|
| | Recycle 1 | Recycle 2 | Recycle 3 | Recycle 4 |
| Pigment of invention Dry blend | 100 | 100 | 99.1 | 98.5 |
| Pigment - untreated Bonded | 100 | 97.4 | 95.7 | 94.4 |

Additionally, the pigment content was determined from samples of the powder spray-out at the initial point and during the fourth recycle. It was found that the percent pearlescent pigment lost after four recycles with the inventive pigment in the dry blend sample was 0.73% while it was 1.11% with the untreated exterior pearlescent pigment of the Benda-Lutz bonded sample.

These results clearly show that the pearlescent pigment of this invention incorporated into powder coating formulations by dry blending has better retention of pigment throughout its spray-out then the industry standard for incorporation of pearlescent pigments into powder coating formulations.

EXAMPLE 9

The following cosmetic powder press patte composition was prepared:

| | |
|---|---|
| Talc | 53.00 |
| Treated Mica of Example 3 | 15.00 |
| Boron Nitride | 7.00 |
| Magnesium Myristate | 5.00 |
| Silica | 2.00 |
| Manganese Violet | 2.20 |
| Iron Oxides | 0.30 |
| Preservatives | 0.50 |
| Treated Pearlescent Pigment of Example 5 | 7.00 |
| Octyl Palmitate | 6.90 |
| Isostearyl Neopentanoate | 1.00 |
| Antioxidant | 0.10 |
| | 100.00 wt % |

The treated mica concentration in a powder formulation can vary from 5–25%. Likewise, the treated pearlescent pigment in a powder formulation could be from 5–40%.

EXAMPLE 10

A lipstick was prepared having the following composition:

| | |
|---|---|
| Lipstick Base (CLL-980109) | 47.05 |
| Treated Mica of Example 3 | 3.00 |
| Tocopheryl Acetate | 0.20 |
| Preservatives | 0.30 |
| Fragrance | 0.10 |
| Treated Pearlescent Pigment of Example 1 | 15.00 |
| Castor Oil | 34.35 |
| | 100.00 wt % |

The amount of treated mica in a lipstick formulation could be from 2–7% and the amount of treated pearlescent pigment could be from 5–15.

EXAMPLE 11

A blush was prepared having the following composition:

| | |
|---|---|
| Talc | 25.40 |
| Treated Mica of Example 3 | 20.00 |
| Zinc Stearate | 3.00 |
| Treated Kaolin of Example 2 | 8.00 |
| Preservatives | 0.50 |
| Treated Pearlescent Pigment of Example 1 | 38.00 |
| Antioxidant | 0.10 |
| Squalane | 3.00 |
| Caprylic/Capric Trygliceride | 2.00 |
| | 100.00 wt % |

The quantity of treated kaolin range in a blush formulation could be from 3–10% and the treated mica could be from 5–25%. Also, the treated pearlescent pigment in a blush formulation could be from 5–40%.

Various changes and modifications can be made in the products and process of the present invention without departing from the spirit and scope thereof. The various embodiments which have been illustrated in this specification were intended to exemplify the invention but were not intended to limit it.

What is claimed is:

1. A lamellar platelet having a hydrophobic surface layer thereon comprising a partly dehydrated metal hydroxide-organic salt composite film.

2. The platelet of claim 1 in which the metal is a Group III metal.

3. The platelet of claim 1 in which the organic salt is selected from the group consisting of alkylsulfate and salts of an amino acid, fatty acid or benzoic acid.

4. The platelet of claim 3 in which the Group III metal is aluminum.

5. The platelet of claim 4 in which the organic salt is selected from the group consisting of lauryl sulfate and salts of lauric acid, sulfanilic acid, L-glutamine or L-phenylalanine.

6. The platelet of claim 1 in which the platelet comprises mica, kaolin or a lamellar metal-containing pigment.

7. The platelet of claim 6 in which the platelet comprises a metal flake or oxide coated-metal flake pigment.

8. The platelet of claim 7 in which the platelet comprises a metal oxide-coated mica pigment.

9. The platelet of claim 8 in which the platelet comprises a titanium or iron oxide-coated mica pigment.

10. A composition comprising an admixture of particulate and particulate pigment in which the pigment is the pigment of claim 9.

11. The composition of claim 10 in which the particulate is a powder coating composition particulate resin carrier.

12. The composition of claim 10 in which the particulate comprises a plastic.

13. The composition of claim 10 in which the particulate comprises a cosmetic ingredient.

14. A composition comprising an admixture of particulate and particulate pigment in which the pigment is the pigment of claim 6.

15. A composition comprising an admixture of particulate and particulate pigment in which the pigment is the pigment of claim 4.

16. A composition comprising an admixture of particulate and particulate pigment in which the pigment is the pigment of claim 2.

17. A composition comprising an admixture of particulate and particulate pigment in which the pigment is the pigment of claim 1.

18. The composition of claim 17 in which the particulate is a powder coating composition particulate resin carrier.

19. The composition of claim 17 in which the particulate comprises a plastic.

20. The composition of claim 17 in which the particulate comprises a cosmetic ingredient.

21. A method of preparing a particulate comprising placing a lamellar platelet and a surface layer gel-forming material under gel forming conditions; combining the resulting positively charged amorphous metal oxide hydrated gel film with a water soluble organic acid or salt; and partly dehydrating the resulting metal oxide-organic salt polymer film to form a hydrophobic metal hydroxide-organic salt composite polymer surface film on said platelet.

22. The method of claim 21 in which the gel-forming material is a metal salt.

23. The method of claim 22 in which the water soluble organic acid or salt is selected from the group consisting of amino acid, fatty acid, benzoic acid and alkylsulfate.

24. The method of claim 22 in which the gel-forming material is a Group III metal salt.

25. The method of claim 24 in which the water soluble organic acid or salt is selected from the group consisting of amino acid, fatty acid, benzoic acid and alkylsulfate.

26. The method of claim 25 in which the Group III metal salt is an aluminum salt.

27. The method of claim 26 in which the water soluble organic acid or salt is selected from the group consisting of lauryl sulfate, lauric acid, sulfanilic acid, L-glutamine and L-phenylalanine.

28. The method of claim 27 in which the lamellar platelet comprises mica, kaolin or a metal-containing pigment.

29. The method of claim 28 in which the metal containing pigment comprises a metal oxide-coated mica pigment.

30. The method of claim 29 in which the lamellar metal-containing pigment comprises a titanium or iron oxide-coated mica pigment.

31. The method of claim 21 in which the metal containing pigment comprises a metal oxide-coated mica pigment.

32. The method of claim 31 in which the lamellar metal-containing pigment comprises a titanium or iron oxide-coated mica pigment.

* * * * *